United States Patent [19]

Pitet et al.

[11] Patent Number: 4,851,411
[45] Date of Patent: Jul. 25, 1989

[54] 5-MONOARYL AS.-TRIAZIN-3-ONES SUBSTITUTED IN 2-POSITION, AND THEIR USE AS MEDICAMENTS

[75] Inventors: Guy Pitet, Toulouse; Henri Cousse; Antoine Stenger, both of Castres; Michel Briley, Noailhac; Philippe Chopin, Castres, all of France

[73] Assignee: Pierre Fabre Medicament, Paris, France

[21] Appl. No.: 4,169

[22] Filed: Jan. 15, 1987

[30] Foreign Application Priority Data

Jan. 16, 1986 [FR] France ................. 86 00552

[51] Int. Cl.[4] .................. A01N 43/707; C07D 253/06
[52] U.S. Cl. ..................................... 514/242; 544/182
[58] Field of Search .................. 544/182; 514/242

[56] References Cited

U.S. PATENT DOCUMENTS 4,511,566 4/1985 Pitet et al. ................... 544/182

OTHER PUBLICATIONS

Rasmussen et al., Chemical Abstracts, vol. 103, entry 141919p (1985).
Sasaki et al., Chemical Abstracts, vol. 94, entry 15685s (1981).

Primary Examiner—John M. Ford
Attorney, Agent, or Firm—Gordon W. Hueschen

[57] ABSTRACT

The present invention concerns new 5-monoaryl as.-triazin-3-ones substituted in 2-position, a method of preparing them, and their use as medicaments.

The compounds according to the present invention have general formula (I)

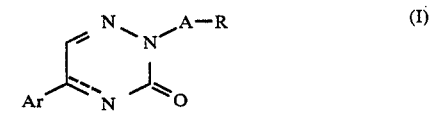

in which:
the bond represented by a dashed line indicates the presence of an optional double bond;
A represents a direct N—C bond, a straight or branched $C_1$ to $C_5$ alkylene, possibly substituted one or more times by —COOR' or by Ar;
R represents —H, —OH,

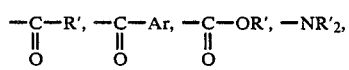

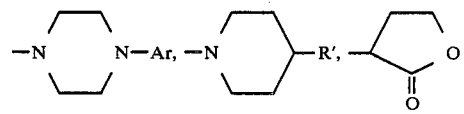

R' represents —H, —OH, straight or branched $C_1$ to $C_7$ alkyl, —$NH_2$;
Ar represents an aromatic ring having 5 or 6 members possibly containing a heteroatom such as O, N, S and possibly substituted one or more times by a radical selected from among —OH, $C_1$ to $C_4$ alkyl, $C_1$ and $C_4$ alkoxy, halogen, —$CF_3$, acetonyloxy,

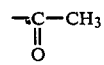

and γ-butyrolactone; as well as their pharmaceutically acceptable salts.

9 Claims, No Drawings

5-MONOARYL AS.-TRIAZIN-3-ONES SUBSTITUTED IN 2-POSITION, AND THEIR USE AS MEDICAMENTS

The present invention, developed at the Pierre Fabre Medicament Research Center, has as its object new as.-triazines which have pharmacological properties and are useful in the treatment of diseases of the central nervous system, such as anxiety or states of depression.

The known as.-triazines which are useful in therapy are exclusively 5,6-diaryls and more particularly compounds of the general formula-

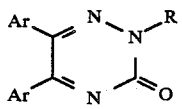

These compounds, which are powerful peripheral analgesics, are described in the following patents of the applicant: FR-A- 2 383 176; FR-A- 2 500 830 and FR-A- 2 544 313.

The present invention concerns 5-monoaryl as.-triazin-3-ones substituted in 2-position, of the general formula I:

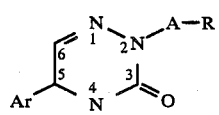

in which:

the bond represented by a dashed line indicates the presence of an elective double bond; when this double bond is not present, the nitrogen and carbon atoms occupying the 4 and 5 positions respectively of the triazine ring are hydrogenated;

A represents a direct N-C bond, a straight or branched $C_1$ to $C_5$ alkylene, possible substituted one or more times by —COOR' or by Ar;

R represents —H, —OH,

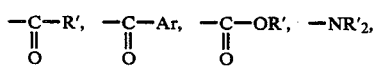

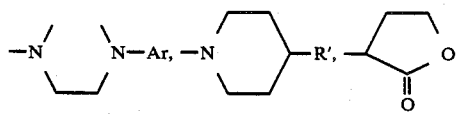

R' represents —H, —OH, straight or branched $C_1$ to $C_7$ alkyl, —NH$_2$;

Ar represents an aromatic ring having 5 or 6 members, possibly containing a heteroatom such as O, N, S, and possibly substituted one or more times by a radical selected from among —OH, $C_1$ to $C_4$ alkyl, $C_1$ to $C_4$ alkoxy, halogen, —CF$_3$, acetonyloxy,

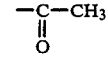

and γ-butyrolactone; as well as their pharmaceutically acceptable salts.

The preferred compounds of the present invention are those of general formula I in which:

Ar represents

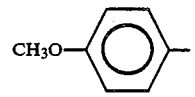

The present invention also concerns a method of preparing compounds of the general formula I which method is characterized by the fact that it is in accord with the following general scheme:

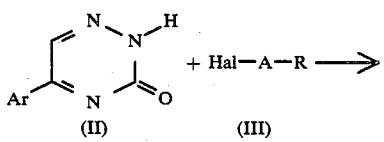

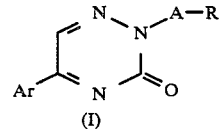

in which A, R and Ar are as defined above,

Hal is a halogen, preferably chlorine or bromine.

This reaction takes place in the presence of a sodating agent of the alkali-metal hydride or amide type. Sodium hydride or sodium amide is preferably used.

This reaction is carried out within a suitable solvent, preferably an organic solvent, such as DMF.

The synthesis intermediaries of general formula (II) can be obtained by various processes known in the prior art. In particular, recourse can be had to the techniques reported in the following articles: R. TRUST et al., Heterocyclic Chemistry 1979, November, page 1393 and W. HEILMAN, J. Med. Chem. 1979, 22 (6), page 671.

As an example of the preparation of compounds of general formula II in which Ar represents

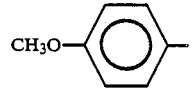

one can proceed in accordance with one of the following two variants:

In accordance with a first variant, the method of synthesis is in accordance with the following scheme:

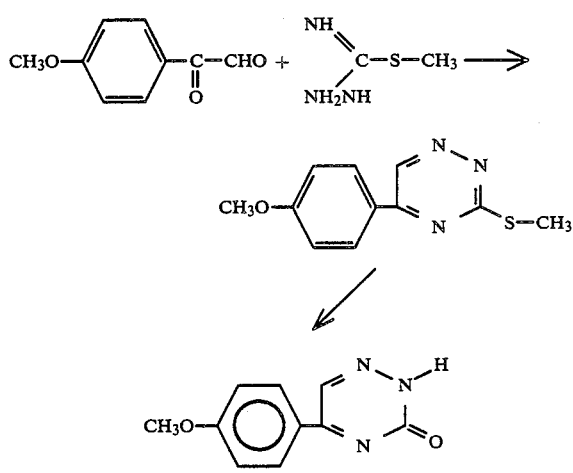

In accordance with this variant, the operating conditions are as follows:

for the synthesis of the p-methoxyphenylglyoxal of the developed formula:

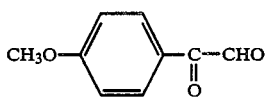

11.1 g of selenium dioxide (namely $10^{-1}$M)
75 ml of dioxane 3 ml of water are placed in a 250 ml round-bottom flask provided with a magnetic agitator and reflux condenser and heated at 80° C. until completely dissolved.

There is then directly added a solution of:

15 g of p-methoxyacetophenone (namely $10^{-1}$M)

20 ml of dioxane and heating is effected for 15 hours under reflux (the solution becomes red immediately upon the addition). It is filtered hot on a Buchner funnel and bed of celite.

For the synthesis of the 3-methylthio 5-p-methoxyphenyl as.-triazine of the developed formula:

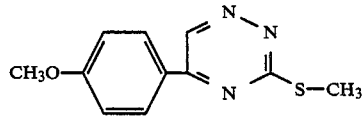

one adds to the filtrate previously obtained:
100 g of crushed ice
12.6 g of sodium bicarbonate (namely $1.5.10^{-1}$M)
31 g of S-methylthiosemicarbazide iodohydride (produced in accordance with D.F. 375).

It is set aside with agitation for one hour. A yellowish-white product precipitates, and it is then set aside overnight in the refrigerator.

It is taken up with methylene chloride, washed with water in a funnel, dried over sodium sulfate, filtered, and concentrated to dryness.

There are obtained 16 g of crystalline product which is recrystallized from 10 parts by volume of 90% ethanol.

The characteristics of the product obtained are:
M.P.: 125° C.

I.R. and N.M.R.: Spectra in agreement with the structure proposed

Yield: 70-80% Finally, for the synthesis of 3-oxo 5-p-methoxyphenyl as.-triazine of the developed formula:

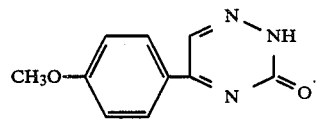

one proceeds in the following manner for an operating unit of $1.7.10^{-2}$M:

Into a 250 ml round-bottom flask provided with magnetic agitation and reflux condenser and having on top a $CaCl_2$ guard tube, there are placed:

4 g of 3-methylthio 5-p-methoxyphenyl as.-triazine
125 ml of ethyl alcohol dried on a sieve
3 g of potassium hydroxide in the form of crushed pellets.

Heating is effected for two hours under reflux. A yellow product precipitates; it is allowed to come to room temperature and then cooled to 0° C. It is dried over fritted glass and washed with ethyl alcohol.

The precipitate is dissolved completely in 100 ml of water and brought to a pH of 1 with concentrated HCl. A white product precipitates.

It is dried over fritted glass, washed until neutral with water, and dried in a vacuum oven in the presence of $P_2O_5$.

The properties of the product obtained are:
M.P.: 260° C. (Köfler stage)
I.R. spectrum in accordance with the structure proposed
Weight: 3.12 g
Yield: 89% (operating units of 2 to $6.10^{-2}$M led to the same yield).

In accordance with a second variant, the method of synthesis of the intermediate compound of general formula II in which:

Ar represents

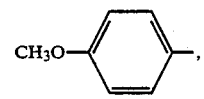

is in accord with the following reaction scheme:

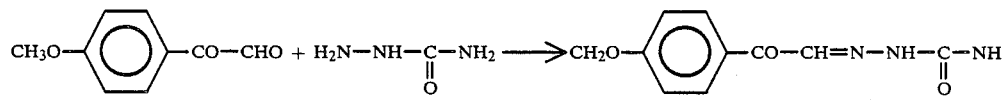

-continued

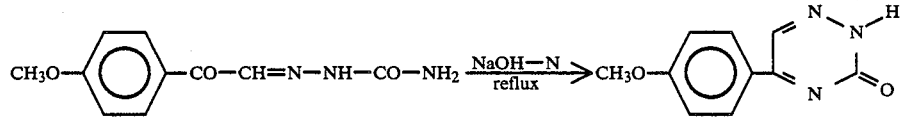

One proceeds in the following manner for an operating unit of $10^{-1}M$:

Into a 250 ml round-bottom flask equipped with a magnetic agitator and a reflux condenser there are introduced:

11.1 g of selenium dioxide (namely $10^{-1}M$)
75 ml of dioxane
3 ml of $H_2O$

Heating is effected to dissolution on an oil bath. A solution of 15 g of p-methoxy acetophenone (namely $10^{-1}M$) in 20 ml of dioxane is added. Heating is effected for 5 hours under reflux. It is filtered hot over a Buchner funnel with celite bed.

There are added to the filtrate, with agitation:
100 g of crushed ice
9 g of $NaHCO_3$
11.1 g of semicarbazide hydrochloride (namely $10^{-1}M$) (EGA).

It is set aside with vigorous agitation for one hour, followed by four hours in the refrigerator. The beige product obtained is dried over fritted glass, washed with a large amount of $H_2O$ and dried in a vacuum oven in the presence of $P_2O_5$.

There are thus obtained, by way of example, 16.5 g of corresponding semicarbazone, which is cyclized by heating under reflux in 200 ml of NaOH (N).

The hot solution is filtered over paper and brought to an acid pH with 25 ml of concentrated HCl.

The 3-oxo p-methoxyphenyl as.-triazine precipitates. It is dried over fritted glass, washed with a large amount of water and dried in a vacuum oven in the presence of $P_2O_5$.

13.5 g of 3-oxo 5-p-methoxyphenyl as.-triazine are obtained, namely a yield of 66%.

Based on toxicological and pharmacodynamic experiments, it is found that the compounds of general formula I have extensive therapeutic activity, particularly in the treatment of disturbances of the central nervous system such as anxiety and/or conditions of depression.

This is why the present invention concerns therapeutic compositions which are useful in particular for the treatment of such disturbances and contain at least one compound of general formula I by way of active principle and a pharmaceutically acceptable excipient by way of support or carrier for the active principle.

The form of administration and the dosage of such pharmaceutical compositions depend on the compound of general formula I selected, on the disease to be treated, and on the opinion of the practitioner.

Finally, the present invention concerns the use of at least one of the compounds of general formula I or their salts for the preparation of pharmaceutical compositions useful for the treatment of diseases of the central nervous system.

The following examples make it possible to illustrate the invention without in any way limiting its scope; they concern, first of all, compounds of general formula I which are particularly preferred and, then, the results of pharmacological experiments carried out on the compounds of general formula I.

EXAMPLE 1

2-acetonyl 3-oxo 5-p-methoxyphenyl ax.-triazine

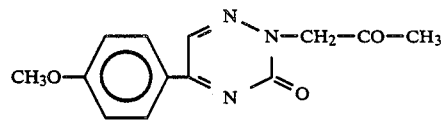

Operating Unit: $10^{-2}M$

In a 100 ml three-neck round-bottom flask provided with mechanical agitation, a feed tube and a potash guard connected to a device making it possible to measure the liberation of hydrogen, there are introduced:

10 ml of anhydrous DMF, previously redistilled and protected from humidity on molecular sieves
0.50 g of HNa (50% dispersion in oil)

There is slowly added through the funnel a suspension of:

2.03 g of 3-oxo 5-p-methoxyphenyl triazine (namely $10^{-2}M$)
(Synthesis No. 377)
50 ml of DMF It is set aside with agitation at room temperature for about one hour until obtaining the theoretical liberation (224 ml) of hydrogen.

There are directly added:
1.38 g of chloroacetone (namely $1.5.10^{-2}M$).

Fluidification of the reaction mixture is noted. It is set aside with agitation for three hours at room temperature. The DMF is concentrated to dryness in a rotary evaporator.

The residue is taken up with 50 ml of water and extracted with $2 \times 25$ ml of $CH_2Cl_2$. The organic phases are dried over $Na_2SO_4$ and concentrated to dryness. There are obtained 3 g of crude product, which is recrystallized from 50 ml of EtOH. After filtration, centrifuging and drying, there are obtained 2.2 g of 2-acetonyl 3-oxo 5-p-methoxyphenyl as.-triazine.

Properties:
MP: 162° C. ±2°

| IR: | |
|---|---|
| $\nu C = O_{triazine}$ | =1660 (wide) |
| $\nu C = O_{ketone}$ | =1730 |

NMR (in accordance with the structure)

Yield: 85%
MCC=toluene/ethyl acetate 7:3
Rf=0.05

In accordance with the same method but condensing the corresponding alkyl halides, there were obtained the following derivatives, illustrating the cases in which R is alkyl, carbonyl and alkyl.

EXAMPLE 2

2-N-acetonyl 3-oxo 5-p-hydroxyphenyl as.-triazine

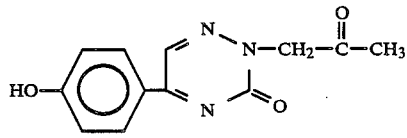

Properties:
Yellow crystals
Melting point: 201° C.
Soluble in the hot, recrystallizes in the cold in alcohols; soluble in dilute aqueous bases; rather soluble in water.
Insoluble in ether, chloroform, benzene.

EXAMPLE 3

2-acetonyl 3-oxo 5-p-(alpha oxy γ butryolactone)phenyl as.-triazine

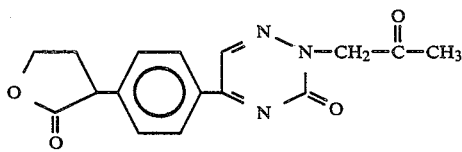

Properties:
White crystals
Melting point: 199° C.
Insoluble in water, benzene, ether, chloroform

EXAMPLE 4

2-alpha-methylacetonyl 3-oxo 5-p-methoxyphenyl as.-triazine

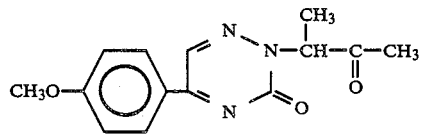

Properties:
Melting point: 158° C.
Beige crystals
Soluble in methylene chloride, chloroform; insoluble in water

EXAMPLE 5

2-(3'-methyl 2'-one butyl) 3-oxo 5-p-methoxyphenyl as.-triazine

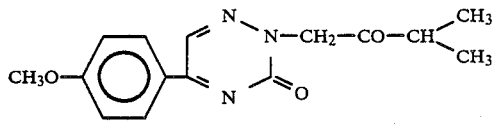

Properties:
Pale yellow crystals
Melting point: 168° C.±2°
Soluble in chloroform, methylene chloride
Insoluble in water, poorly soluble in benzene and ether

EXAMPLE 6

2-acetonyl 3-oxo 5-p-methylphenyl as.-triazine

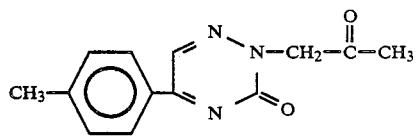

Properties:
Beige crystals
Melting point: 171° C.
Soluble in chloroform, methylene chloride; insoluble in water, ether

EXAMPLE 7

2-acetonyl 3-oxo 5-phenyl as.-triazine

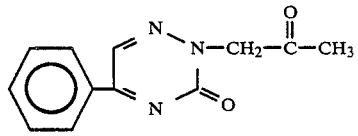

Properties:
Beige crystals
Melting point: 143° C.
Soluble in chloroform, methylene chloride; insoluble in water, ether

EXAMPLE 8

2-(3'-propyl 2'-one hexanyl) 3-oxo 5-p-methylphenyl as.-triazine

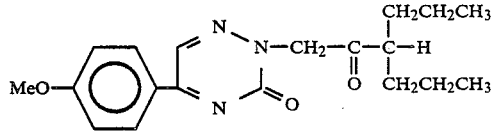

Properties:
Aged-white crystals
Melting point: 181° C.
Soluble in chloroform, methylene chloride; insoluble in water In the same way, upon treating with an alkyl halide, for example CH$_3$X, the compound of Example 9 obtained illustrates the case in which R=alkyl.

EXAMPLE 9

2-methyl 3-oxo 5-p-acetonoxyphenyl as.-triazine

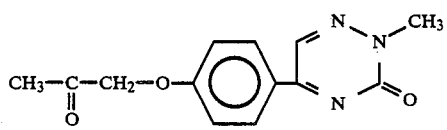

Properties:
Beige crystals
Melting point: 181° C.
Soluble in aqueous dilute acids and in methylene chloride; insoluble in water, chloroform By operating as previously but treating the triazine intermediaries with compounds of the formula

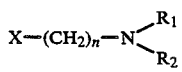

we obtained the following compounds:

EXAMPLE 10

2 β ethyl(metachlorophenyl)piperazine 3-oxo 5-p-methoxyphenyl as.-triazine

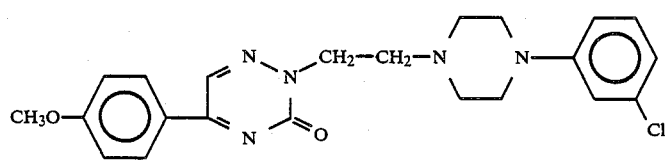

Properties:
White crystals
Melting point: 183° C.
Soluble in the hot in aqueous dilute acids
Poorly soluble in chloroform, methylene chloride

EXAMPLE 11

2-γ propyl p-piperazinoacetophenone 3-oxo 5-methylphenyl as.-triazine

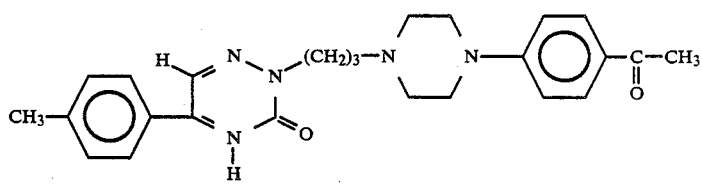

Properties:
Yellow crystals
Melting point: 141° C.
Soluble in the hot in alcohols, chloroform, methylene chloride; insoluble in water, alcohol, ether

EXAMPLE 12

2-N-γ propyl(m-chlorophenylpiperazine) 3-oxo 4,5-dihydro 5-p-methoxyphenyl as.-triazine

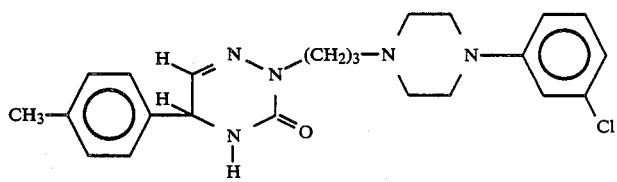

Properties:
White crystals
Melting point: 130° C.
Soluble in chloroform, methylene chloride, in the hot in aqueous dilute acids and in alcohols; insoluble in water, ether

EXAMPLE 13

2-N-δ butyl (m-chlorophenyl piperazine) 3-oxo 5-p-methylphenyl as.-triazine

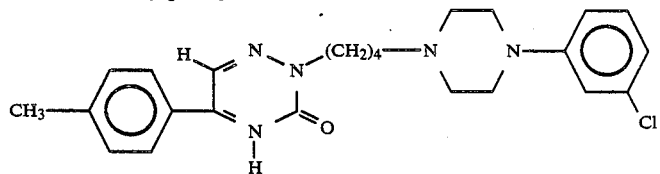

Properties:
Beige crystals
Melting point: 162° C.

Soluble in chloroform, methylene chloride; in the hot in aqueous dilute acids and alcohols; insoluble in water, ether

EXAMPLE 14

2-γ(m-chlorophenylpiperazine)-propyl 3-oxo 5-p-methylphenyl as.-triazine hydrochloride

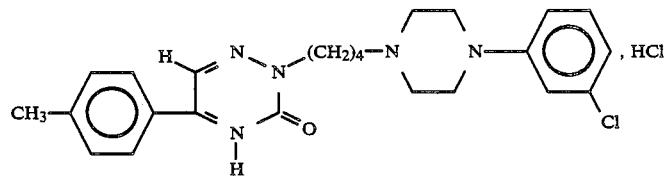

Properties:
White crystals
Melting point: abt. 230° C.
Soluble in chloroform, methylene chloride; insoluble in water, ether

EXAMPLE 15

2-N (ε-pentyl m-chlorophenyl piperazine) 3-oxo 5-p-methoxyphenyl as.-triazine

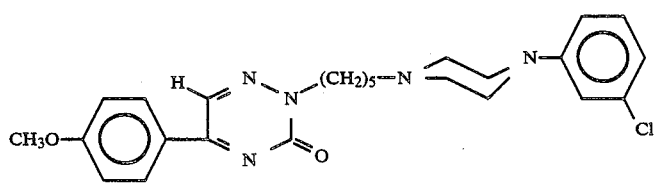

Properties:
Beige crystals
Melting point: 110° C.
Soluble in chloroform, methylene chloride; insoluble in water, ether

EXAMPLE 16

2-β ethyl (m-trifluoromethylphenyl) piperazine 3-oxo 5-p-methoxyphenyl as.-triazine

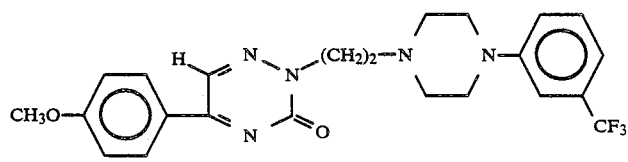

Properties:
Beige crystals
Melting point: 168° C.
Soluble in chloroform, methylene chloride; poorly soluble in benzene; insoluble in water, ether

EXAMPLE 17

2-γ dimethylaminopropyl 3-oxo 5-p-methoxyphenyl as.-triazine

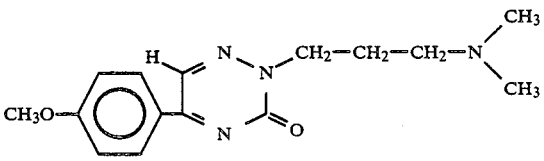

Properties:
Beige crystals
Melting point: 102° C.
Soluble in chloroform, methylene chloride, benzene, alcohols, aqueous dilute acids; insoluble in ether, water By way of illustration and not of limitation we may cite a few derivatives which illustrate various functionalized R substituents, namely alcohol-acids in 2 position.

EXAMPLE 18

2-[3-(3-carboxy 1-propanol)] 3-oxo 5-p-methoxyphenyl as.-triazine

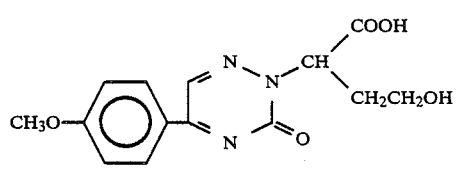

Properties:
Pale yellow crystals
Melting point: 190° C. decomposition
Poorly soluble in chloroform, methylene chloride; rather soluble in alcohols; insoluble in water

EXAMPLE 19

2-[3-(3-carboxy 1-propanol)] 3-oxo 5-p-methylphenyl as.-triazine

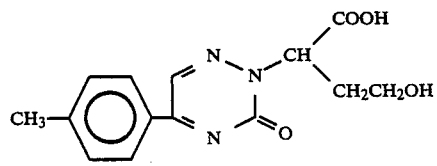

Properties:
Pale yellow crystals
Melting point: 180° C. decomposition
Poorly soluble in alcohols, benzene, chloroform; insoluble in water, ether
The corresponding lactones:

EXAMPLE 20

2-butyrolactone 3-oxo 5-p-methylphenyl as.-triazine

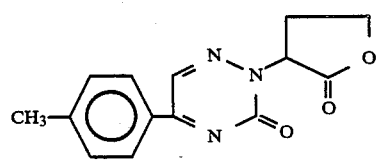

Properties:
Pale beige crystals
Melting point: 185° C. (EtOH)
Soluble in chloroform, methylene chloride; poorly soluble in ether, benzene; insoluble in water obtained from the compound of Example 19, in acid medium.

EXAMPLE 21

2-γ-butyrolactone 3-oxo 5-p-methoxyphenyl as.-triazine

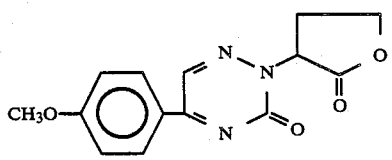

Properties:
Pale yellow crystals
Melting point: 194° C. (DMF)
Soluble in chloroform, methylene chloride; poorly soluble in benzene, alcohols; insoluble in water This product was obtained from 5-p-methoxyphenyl as.-triazine by activation of the 2 nitrogen of the triazine ring by means of sodium hydride in DMF and then condensation with α-bromobutyrolactone in the same medium.

The previous examples have illustrated the case of Ar, para phenyl group substituted by a methyl or methoxy group; the following examples supplement the different meanings forming the object of the present invention:

*unsubstituted phenyl (Example 22)
*orthomethoxy phenyl (Example 23)
*p-ethoxyphenyl (Example 24)
*2',4'-dimethoxy phenyl (Example 25)

EXAMPLE 22

2-(3-methyl-2-one butyl) 5-phenyl as.-triazine

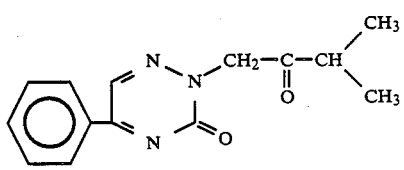

Properties:
Beige crystals
Melting point: 174° C.
Soluble in chloroform, methylene chloride; soluble in the hot in alcohols; insoluble in water

EXAMPLE 23

2-acetonyl 3-oxo 5-o-methoxyphenyl as.-triazine

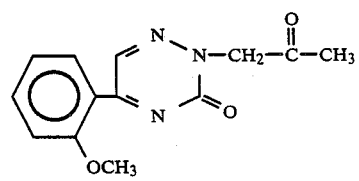

Properties:
Beige crystals
Melting point 125° C.
Soluble in chloroform, methylene chloride; insoluble in water, ether

EXAMPLE 24

2-acetonyl 3-oxo 5-p-ethoxyphenyl as.-triazine

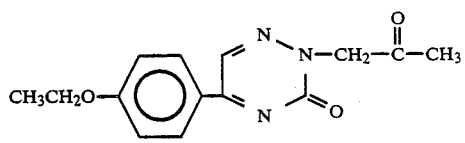

Properties:
White crystals
Melting point: 162° C.
Soluble in chlorinated solvents; insoluble in water, ether; soluble in the hot in alcohols

EXAMPLE 25

2-acetonyl 3-oxo 5-(2',4'-dimethoxy)phenyl as.-triazine

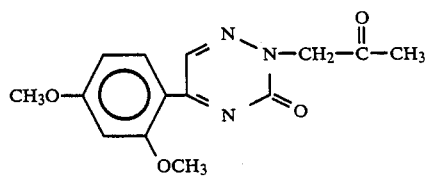

Properties:
Beige crystals
Melting point: 140° C.

Soluble in chloroform, methylene chloride; insoluble in water, ether

EXAMPLE 26

2-acetonyl 3-oxo 5-γ-thienyl as.-triazine

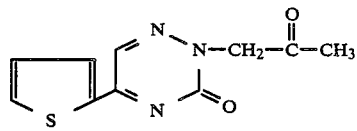

Properties:
Orange crystals
Melting point: 160° C.
Soluble in chlorinated solvents; insoluble in water, ether Finally, the last examples illustrate differently functionalized R substituents:

EXAMPLE 27

2-diethoxysuccinyl 3-oxo 5-p-methoxyphenyl as.-triazine

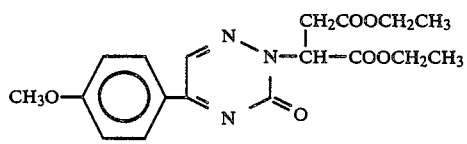

Properties:
White crystals
Melting point: 78° C.
Soluble in benzene, alcohols, chloroform; insoluble in water

EXAMPLE 28

N 2-[ε-pentyl (4-hydroxypiperidine)] 3-oxo 5-p-methoxyphenyl as.-triazine

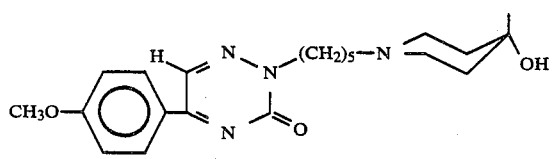

Properties:
Beige crystals
Melting point: 114° C.
Soluble in alcohols, chloroform; insoluble in water

EXAMPLE 29

N-2[α(1,2-diphenylethan 1-ol)] 3-oxo 4,5-dihydro 5-p-methylphenyl as.-triazine

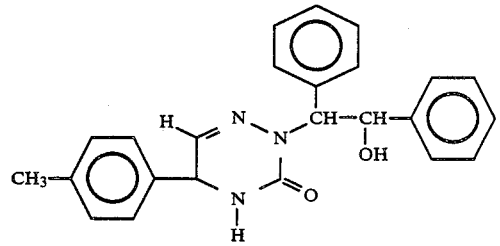

Properties:
White crystals
Melting point: 214° C.
Soluble in alcohols in the hot; insoluble in water, ether, chloroform

EXAMPLE 30

2-N-diphenylmethyl 3-oxo 5-p-methoxyphenyl as.-triazine

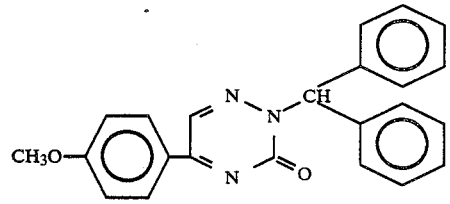

Properties:
Beige crystals
Melting point: 193° C.
Soluble in hot alcohols, methylene chloride; insoluble in water, chloroform

EXAMPLE 31

2-ethanol 3-oxo 5-p-methoxyphenyl as.-triazine

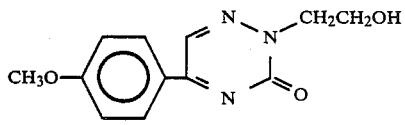

Properties:
Beige crystals
Melting point: 134° C.
Soluble in the hot in water, poorly soluble in chloroform; insoluble in benzene, ether; rather soluble in methylene chloride

EXAMPLE 32

2-N-acetamido 3-oxo 5-p-methoxyphenyl as.-triazine

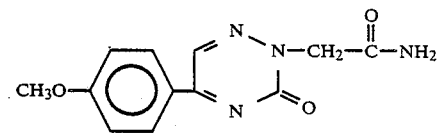

Properties:
Yellow crystals

EXAMPLE 33

2-N-(γp-fluorobutyrophenone) 3-oxo 5-p-methoxyphenyl as.-triazine

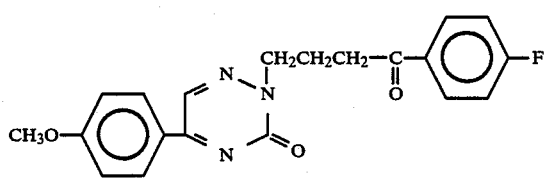

Properties:
White crystals
Melting point: 156° C.
Soluble in chloroform, methylene chloride; insoluble in water

EXAMPLE 34

2-N-desyl 3-oxo 5-p-methoxyphenyl as.-triazine

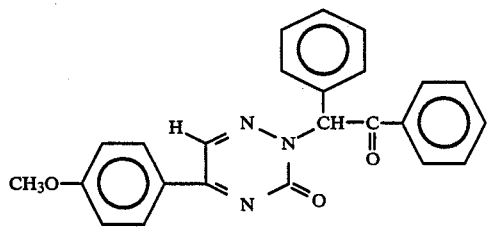

Properties:
Beige crystals
Melting point: 190° C.
Soluble in the hot in alcohols; rather soluble in chloroform; poorly soluble in ether; insoluble in water

EXAMPLE 35

2-N-ethylbutyrate 3-oxo 5-p-methylphenyl as.-triazine

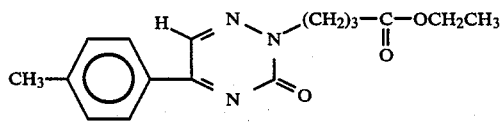

Properties:
White crystals
Melting point: 52° C.
Soluble in benzene, alcohols, chloroform; insoluble in water

EXAMPLE 36

2-N-desyl 3-oxo 5-p-methylphenyl as.-triazine

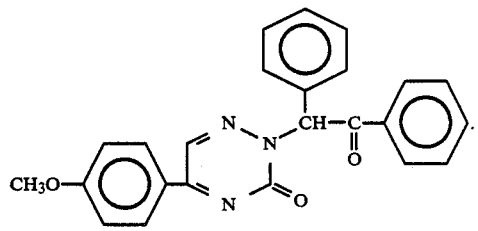

Properties:
Pale yellow crystals
Melting point: 215° C.
Soluble in alcohols in the hot, chloroform, methylene chloride; insoluble in water

EXAMPLE 37

2-Phenacyl 3-oxo 5-p.methoxyphenyl as triazine

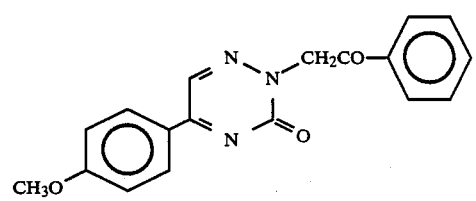

Characteristics:
Melting point: 210° C.
Soluble in acetic acid; insoluble in water

EXAMPLE 38

2-p.methylphenacyl 3-oxo 5-p.methoxyphenyl as triazine

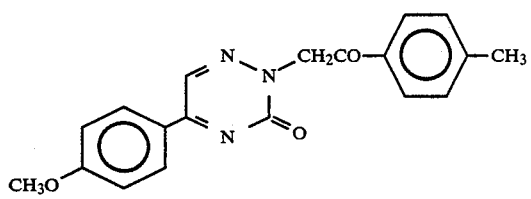

Characteristics:
Melting point: 196° C.
Soluble in acetic acid
Insoluble in water and in alcohols

EXAMPLE 39

2-(dichloro-2,4 phenacyl) 3-oxo 5-p.methoxyphenyl as triazine

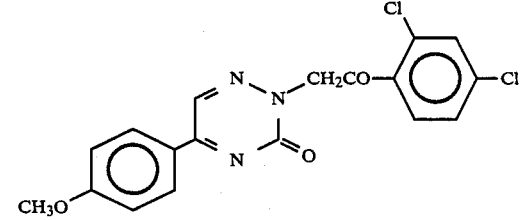

Characteristics:
Melting point: 192° C.
Soluble in acetic acid
Insoluble in water and in alcohols

EXAMPLE 40

2-p.methoxyphenacyl 3-oxo 5-p.methoxyphenyl as triazine

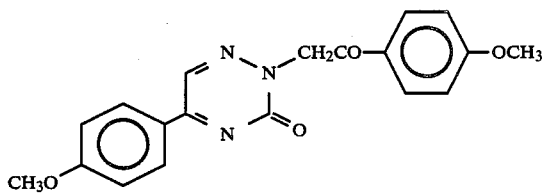

Characteristics:
Melting point: 220° C.
Insoluble in water, acetic acid, and alcohols

EXAMPLE 41

2-(oxo-2' butyl) 3-oxo 5-p.methoxyphenyl as triazine

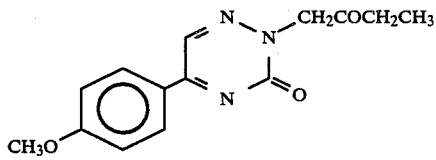

Characteristics:
Melting point: 152° C.
Soluble in acetic acid
Insoluble in water and alcohols

PHARMACOLOGICAL EXPERIMENTS (a) Toxicology

The toxicity study was carried out in the conventional mouse, weighing about 20 g.

The substances were administered orally in a single dose of 300 and 1000 mg/kg respectively. At these doses we were not able to determine the $LD_{50}$'s which are higher >1000 mg/kg. By way of example, for the compound of Example 1, the $LD_{50}$ is greater than 3000 mg/kg.

(b) Action on the central nervous system

The tests used for the pharmacological screening are:
the potentialization of 5 HTP (Ref.: Christensen, A. V. et al., Eur. J. of Pharm. (1977), 41, 153–162)
the potentialization of l-DOPA (Ref.: Turner and Hebborn, Screening methods in Pharmacology, Vol. II (1971) Academic Press (New York and London)).

The results for a few derivatives among the most active ones are given in the following table:

| Compound of Example No. | Potentialization 5 HTP $ED_{50}$ in mg/kg | Potentialization l-DOPA $LD_{50}$ salivation |
| --- | --- | --- |
| 1 | 25 | 50 |
| 4 | 35 | 60 |
| 9 | 40 | 100 |
| 21 | 27 | 70 |

-continued

| Compound of Example No. | Potentialization 5 HTP $ED_{50}$ in mg/kg | Potentialization l-DOPA $LD_{50}$ salivation |
| --- | --- | --- |
| 23 | 50 | 85 |
| 32 | 20 | 25 |

These compounds were also studied in order to test for anxiolytic activity using a group of tests (Ref.: LAB-X: Sh. Pellow, Ph. Chopin, S. E. File and M. Briley—Validation of open:closed arm entries in an elevated plus-maze as a measure of anxiety in the rat (Journal of Neuroscience Methods, 14 (1983), 149–167)

SKINNER: GELLER and SEIFTER, Psychopharmacologia (1960) 1, 482–492

VOGEL: VOGEL J. R., BEER B., CLODY D. E., Psychopharmacologia (1971), 21 1–7); the compounds were tested at 30 mg/kg by mouth; significant results were found for the compounds of Examples 1, 4, 9, 21 and 22.

In conclusion, with respect to the therapeutic applications, pharmaceutical compositions of the present invention, based on the effects observed in pharmacology and the very low toxicity of the most active compounds and more particularly the compounds of Examples 1, 4, 21 and 32, can be used to treat disturbances related to anxiety and/or states of depression.

These compounds are furthermore without sedative effect, which makes them particularly suitable as compared with diazepinic anxiolytics.

It is to be understood that the invention is not to be limited to the exact details of operation, or to the exact compositions, methods, procedures, or embodiments shown and described, as obvious modifications and equivalents will be apparent to one skilled in the art, and the invention is therefore to be limited only by the full scope which can be legally attributed to the appended claims.

We claim:

1. 5-monoaryl as.-triazin-3-one substituted in 2-position selected from compounds of formula I:

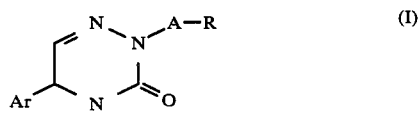

in which:
the bond represented by the dashed line indicates the presence of an optional double bond;
A represents a direct N-C bond (C being the first atom of the group R), a straight or branched $C_1$ to $C_5$ alkylene, possibly substituted one or two times by —COOR' or by Ar;
R represents —H, —OH,

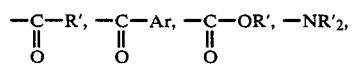

-continued

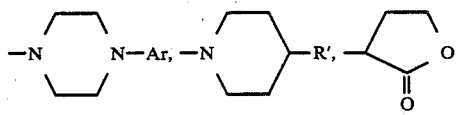

R' represents —H, —OH, straight or branched C₁ to C₇ alkyl, —NH₂;

Ar represents an aromatic ring having 5 or 6 members, possibly containing heteroatom selected from O, N, and S, and possibly substituted one or two times by a radical selected from among —OH, C₁ to C₄ lower alkyl, C₁ to C₄ alkoxy, halogen, —CF₃, acetonyloxy,

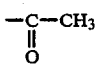

and γ-butyrolactone, and their pharmaceutically-acceptable salts, provided that Ar may not be unsubstituted phenyl or lower-alkylphenyl when —A—R is unsubstituted lower-alkyl or benzyl.

2. 5-monoaryl as.-triazin-3-one substituted in 2-position, according to claim 1, of general formula I, in which
Ar represents

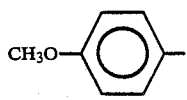

3. A chemical compound according to claim 1 selected from:
2-acetonyl 3-oxo 5-p-methoxyphenyl as.-triazine
2-N-acetonyl 3-oxo 5-p-hydroxyphenyl as.-triazine
2-acetonyl 3-oxo 5-p-(α-oxo-γ-butyrolactonebutyrolacton)phenyl as.-triazine
2-α-methylacetonyl 3-oxo 5-p-methoxyphenyl as.-triazine
2-(3'-methyl-2'-one butyl) 3-oxo 5-p-methoxyphenyl as.-triazine
2-acetonyl 3-oxo 5-p-methylphenyl as.-triazine
2-acetonyl 3-oxo 5-phenyl as.-triazine
2-(3'-propyl-2'-one hexyl) 3-oxo 5-p-methoxyphenyl as.-triazine
2-methyl 3-oxo 5-p-acetonoxyphenyl as.-triazine
2-β-ethyl(metachlorophenyl)piperazine 3-oxo 5-p-methoxyphenyl as.-triazine
2-γ-propyl p-piperazinoacetophenone 3-oxo 5-p-methylphenyl as.-triazine
2-N-γ-propyl (m-chlorophenylpiperazine) 3-oxo 4,5-dihydro 5-p-methoxyphenyl as.-triazine
2-N-δ-butyl (m-chlorophenylpiperazine) 3-oxo 5-p-methylphenyl as.-triazine
2-γ-(m-chlorophenylpiperazine)propyl 3-oxo 5-p-methylphenyl as.-triazine hydrochloride
2-N-(ε-pentyl m-chlorophenyl piperazine) 3-oxo 5-p-methoxyphenyl as.-triazine
2-β-ethyl (m-trifluoromethylphenyl)piperazine 3-oxo 5-p-methoxyphenyl as.-triazine
2-γ-dimethylaminopropyl 3-oxo 5-p-methoxyphenyl as.-triazine 2-[3-(3-carboxy 1-propanol)] 3-oxo 5-p-methoxyphenyl as.-triazine
2-[3-(3-carboxy 1-propanol)] 3-oxo 5-p-methylphenyl as.-triazine
2-butyrolactone 3-oxo 5-p-methoxyphenyl as.-triazine
2-γ-butyrolactone 3-oxo 5-p-methoxyphenyl as.-triazine
2-(3-methyl-2-one butyl) 5-phenyl as.-triazine
2-acetonyl 3-oxo 5-o-methoxyphenyl as.-triazine
2-acetonyl 3-oxo 5-p-ethoxyphenyl as.-triazine
2-acetonyl 3-oxo 5-(2',4'-dimethoxy)phenyl as.-triazine
2-acetonyl 3-oxo 5-α-thienyl as.-triazine
2-diethoxysuccinyl 3-oxo 5-p-methoxyphenyl as.-triazine
2-phenacyl 3-oxo 5-p.methoxyphenyl as triazine
2-p.methylphenacyl 3-oxo 5-p.methoxyphenyl as triazine
2-(dichloro-2,4 phenacyl 3-oxo 5-p.methoxyphenyl as triazine
2-p.methoxyphenacyl 3-oxo 5-p.methoxyphenyl as triazine
2-(oxo-2' butyl) 3-oxo 5-p.methoxyphenyl as triazine
2-N-[ε-pentyl-(4-hydroxypiperidine)] 3-oxo 5-p-methoxyphenyl as.-triazine
2-N-[α(1,2-diphenylethan-1-ol)] 3-oxo 4,5-dihydro 5-p-methylphenyl as.-triazine
2-N-diphenylmethyl 3-oxo 5-p-methoxyphenyl as.-triazine
2-ethanol 3-oxo 5-p-methoxyphenyl as.-triazine
2-N-acetamido 3-oxo 5-p-methoxyphenyl as.-triazine
2-N-(γ-p-fluorobutyrophenone) 3-oxo 5-p-methoxyphenyl as.-triazine
2-N-desyl 3-oxo 5-p-methoxyphenyl as.-triazine
2-N-ethylbutyrate 3-oxo 5-p-methylphenyl as.-triazine
2-N-desyl 3-oxo 5-p-methylphenyl as.-triazine.

4. Pharmaceutical compositions useful for the treatment of anxiety or states of depression comprising, by way of active principle, at least one compound, which is a 5-monaryl as.-triazin-3-one substituted in 2-position selected from compounds of formula I:

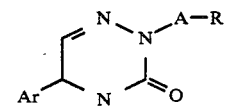

in which:
the bond represented by the dashed line indicates the presence of an optional double bond;
A represents a direct N-C bond (C being the first atom of the group R), a straight or branched C₁ to C₅ alkylene, possibly substituted one or two times by —COOR' or by Ar;
R represents —H, —OH,

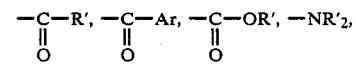

-continued

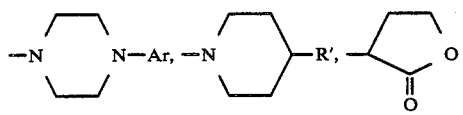

R' represents —H, —OH, straight or branched C₁ to C₇ alkyl, —NH₂;

Ar represents an aromatic ring having 5 or 6 members, possibly containing heteroatom selected from O, N, and S, and possibly substituted one or two times by a radical selected from among —OH, C₁ to C₄ alkyl, C₁ to C₄ alkoxy, halogen, —CF₃, acetonyloxy, $$-\underset{\underset{O}{\|}}{C}-CH_3$$

and γ-butyrolactone, and their pharmaceutically-acceptable salts, and by way of support or vector a pharmaceutically-acceptable excipient.

5. Pharmaceutical composition of claim 4 wherein Ar represents

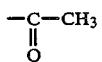

6. Pharmaceutical composition of claim 4 wherein the compound is selected from:
   2-acetonyl 3-oxo 5-p-methoxyphenyl as.-triazine
   2-N-acetonyl 3-oxo 5-p-hydroxyphenyl as.-triazine
   2-acetonyl 3-oxo 5-p-(α-oxy-γ-butyrolacton)phenyl as.-triazine
   2-α-methylacetonyl 3-oxo 5-p-methoxyphenyl as.-triazine
   2-(3'-methyl-2'-one butyl) 3-oxo 5-p-methoxyphenyl as.-triazine
   2-acetonyl 3-oxo 5-p-methylphenyl as.-triazine
   2-acetonyl 3-oxo 5-phenyl as.-triazine
   2-(3'-propyl-2'-one hexyl) 3-oxo 5-p-methoxyphenyl as.-triazine
   2-methyl 3-oxo 5-p-acetonoxyphenyl as.-triazine
   2-β-ethyl (metachlorophenyl)piperazine 3-oxo 5-p-methoxyphenyl as.-triazine
   2-γ-propyl p-piperazinoacetophenone 3-oxo 5-p-methylphenyl as.-triazine
   2-N-γ-propyl (m-chlorophenylpiperazine) 3-oxo 4,5-dihydro 5-p-methoxyphenyl as.-triazine
   2-N-δ-butyl (m-chlorphenylpiperazine) 3-oxo 5-p-methylphenyl as.-triazine
   2-γ(m-chlorophenylpiperazine)propyl 3-oxo 5-p-methylphenyl as.-triazine hydrochloride
   2-N-(ε-pentyl m-chlorophenyl piperazine) 3-oxo 5-p-methoxyphenyl as.-triazine
   2-β-ethyl(m-trifluoromethylphenyl)piperazine 3-oxo 5-p-methoxyphenyl as.-triazine
   2-γ-dimethylaminopropyl 3-oxo 5-p-methoxyphenyl as.-triazine
   2-[3-(3-carboxy 1-propanol)] 3-oxo 5-p-methoxyphenyl as.-triazine
   2-[3-(3-carboxy 1-propanol)] 3-oxo 5-p-methylphenyl as.-triazine
   2-butyrolactone 3-oxo 5-p-methylphenyl as.-triazine
   2-γ-butyrolactone 3-oxo 5-p-methoxyphenyl as.-triazine
   2-(3-methyl-2-one butyl) 5-phenyl as.-triazine
   2-acetonyl 3-oxo 5-o-methoxyphenyl as.-triazine
   2-acetonyl 3-oxo 5-p-ethoxyphenyl as.-triazine
   2-acetonyl 3-oxo 5-(2',4'-dimethoxy)phenyl as.-triazine
   2-acetonyl 3-oxo 5-α-thienyl as.-triazine
   2-diethoxysuccinyl 3-oxo 5-p-methoxyphenyl as.-triazine
   2-phenacyl 3-oxo 5-p.methoxyphenyl as. triazine
   2-p.methylphenacyl 3-oxo 5-p.methoxyphenyl as. triazine
   2-(dichloro-2,4 phenacyl 3-oxo 5-p.methoxyphenyl as. triazine
   2-p.methoxyphenacyl 3-oxo 5-p.methoxyphenyl as. triazine
   2-(oxo-2' butyl) 3-oxo 5-p.methoxyphenyl as. triazine
   2-N-[ε-pentyl-(4-hydroxypiperidine)] 3-oxo 5-p-methoxyphenyl as.-triazine
   2-N-[α(1,2-diphenylethan-1-ol)] 3-oxo 4,5-dihydro 5-p-methylphenyl as.-triazine
   2-N-diphenylmethyl 3-oxo 5-p-methoxyphenyl as.-triazine
   2-ethanol 3-oxo 5-p-methoxyphenyl as.-triazine
   2-N-acetamido 3-oxo 5-p-methoxyphenyl as.-triazine
   2-N-(γ-p-fluorobutyrophenone) 3-oxo 5-p-methoxyphenyl as.-triazine
   2-N-desyl 3-oxo 5-p-methoxyphenyl as.-triazine
   2-N-ethylbutyrate 3-oxo 5-p-methylphenyl as.-triazine, and
   2-N-desyl 3-oxo 5-p-methylphenyl as.-triazine.

7. The method of treating anxiety or states of depression which comprises the step of administering to a subject in need of such treatment an amount of a compound, which is a 5-monoaryl as.-triazin-3-one substituted in 2-position selected from compounds of formula I:

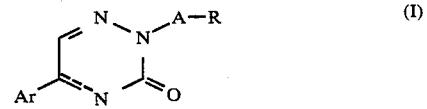

in which:
   the bond represented by the dashed line indicates the presence of an optional double bond;
   A represents a direct N-C bond (C being the first atom of the group R), a straight or branched C₁ to C₅ alkylene, possibly substituted one or two times by —COOR' or by Ar;
   R represents —H, —OH,

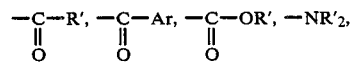

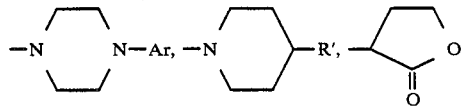

R' represents —H, —OH, straight or branched C₁ to C₇ alkyl, —NH₂;
Ar represents an aromatic ring having 5 or 6 members, possibly containing heteroatom selected from O, N, and S, and possibly substituted one or two times by a radical selected from among —OH, $C_1$ to $C_4$ alkyl, $C_1$ to $C_4$ alkoxy, halogen, —$CF_3$, acetonyloxy,

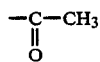

and γ-butyrolactone and their pharmaceutically-acceptable salts, which is effective for the alleviation of such disease.

8. Method of claim 7 wherein Ar represents

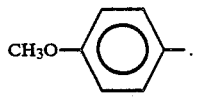

9. Method of claim 7 wherein the compound is selected from
2-acetonyl 3-oxo 5-p-methoxyphenyl as.-triazine
2-N-acetonyl 3-oxo 5-p-hydroxyphenyl as.-triazine
2-acetonyl 3-oxo 5-p-(α-oxy-γ-butyrolacton)phenyl as.-triazine
2-α-methylacetonyl 3-oxo 5-p-methoxyphenyl as.-triazine
2-(3'-methyl-2'-one butyl) 3-oxo 5-p-methoxyphenyl as.-triazine
2-acetonyl 3-oxo 5-p-methylphenyl as.-triazine
2-acetonyl 3-oxo 5-phenyl as.-triazine
2-(3'-propyl-2'-one hexyl) 3-oxo 5-p-methoxyphenyl as.-triazine
2-methyl 3-oxo 5-p-acetonoxyphenyl as.-triazine
2-β-ethyl (metachlorophenyl)piperazine 3-oxo 5-p-methoxyphenyl as.-triazine
2-γ-propyl p-piperazinoacetophenone 3-oxo 5-p-methylphenyl as.-triazine
2-N-γ-propyl (m-chlorophenylpiperazine) 3-oxo 4,5-dihydro 5-p-methoxyphenyl as.-triazine
2-N-δ-butyl (m-chlorphenylpiperazine) 3-oxo 5-p-methylphenyl as.-triazine
2-γ(m-chlorophenylpiperazine)propyl 3-oxo 5-p-methoxyphenyl as.-triazine hydrochloride
2-N-(ε-pentyl m-chlorophenyl piperazine) 3-oxo 5-p-methoxyphenyl as.-triazine
2-β-ethyl (m-trifluoromethylphenyl)piperazine 3-oxo 5-p-methoxyphenyl as.-triazine
2-γ-dimethylaminopropyl 3-oxo 5-p-methoxyphenyl as.-triazine
2-[3-(3-carboxy 1-propanol)] 3-oxo 5-p-methoxyphenyl as.-triazine
2-[3-(3-carboxy 1-propanol)] 3-oxo 5-p-methylphenyl as.-triazine
2-butyrolactone 3-oxo 5-p-methylphenyl as.-triazine
2-γ-butyrolactone 3-oxo 5-p-methoxyphenyl as.-triazine
2-(3-methyl-2-one butyl) 5-phenyl as.-triazine
2-acetonyl 3-oxo 5-o-methoxyphenyl as.-triazine
2-acetonyl 3-oxo 5-p-ethoxyphenyl as.-triazine
2-acetonyl 3-oxo 5-(2',4'-dimethoxy)phenyl as.-triazine
2-acetonyl 3-oxo 5-α-thienyl as.-triazine
2-diethoxysuccinyl 3-oxo 5-p-methoxyphenyl as.-triazine
2-phenacyl 3-oxo 5-p.methoxyphenyl as. triazine
2-p.methylphenacyl 3-oxo 5-p.methoxyphenyl as. triazine
2-(dichloro-2,4 phenacyl 3-oxo 5-p.methoxyphenyl as. triazine
2-p.methoxyphenacyl 3-oxo 5-p.methoxyphenyl as. triazine
2-(oxo-2' butyl) 3-oxo 5-p.methoxyphenyl as. triazine
2-N-[ε-pentyl-(4-hydroxypiperidine)] 3-oxo 5-p-methoxyphenyl as.-triazine
2-N-[α(1,2-diphenylethan-1-ol)] 3-oxo 4,5-dihydro 5-p-methylphenyl as.-triazine
2-N-diphenylmethyl 3-oxo 5-p-methoxyphenyl as.-triazine
2-ethanol 3-oxo 5-p-methoxyphenyl as.-triazine
2-N-acetamido 3-oxo 5-p-methoxyphenyl as.-triazine
2-N-[γ-p-fluorobutyrophenone) 3-oxo 5-p-methoxyphenyl as.-triazine
2-N-desyl 3-oxo 5-p-methoxyphenyl as.-triazine
2-N-ethylbutyrate 3-oxo 5-p-methylphenyl as.-triazine, and
2-N-desyl 3-oxo 5-p-methylphenyl as.-triazine.

* * * * *

UNITED STATES PATENT AND TRADEMARK OFFICE
CERTIFICATE OF CORRECTION

PATENT NO. : 4,851,411

DATED : July 25, 1989

INVENTOR(S) : Guy Pitet, Henri Cousse, Antoine Stenger, Michel Briley, Philippe Chopin It is certified that error appears in the above-identified patent and that said Letters Patent is hereby corrected as shown below:

```
Title Page [57] Abstract, "and" should read -- to --
Col. 1, line 15; "formula-" should read -- formula: --
Col. 3, line 56; "1.5.10" should read -- 1.5·10 --
Col. 4, line 12; start new paragraph with "Finally"
Col. 4, line 24; "1.7.10" should read -- 1.7·10 --
Col. 4, line 49; "6.10" should read -- 6·10 --
Col. 6, line 47; "1.5.10" should read -- 1.5·10 --
Col. 21, line 42; "tonebutyrolacton)" should read -- tone) --
Col. 22, line 6; "-methoxyphenyl" should read -- methylphenyl --
Col. 23, line 54; "m-chlorphenyl" should read -- m-chlorophenyl --

Col. 25, line 45; "(m-chlorphenyl" should read -- (m-chlorophenyl --
Col. 26, line 2; "methoxyphenyl" should read -- methylphenyl --
```

Signed and Sealed this

Tenth Day of July, 1990

Attest:

HARRY F. MANBECK, JR.

*Attesting Officer*  *Commissioner of Patents and Trademarks*

UNITED STATES PATENT AND TRADEMARK OFFICE
CERTIFICATE OF CORRECTION

PATENT NO. : 4,851,411

DATED : July 25, 1989

INVENTOR(S) : Guy Pitet, Henri Cousse, Antoine Stenger, Michel Briley and Philippe Chopin It is certified that error appears in the above-identified patent and that said Letters Patent is hereby corrected as shown below:

Col. 10, approximately line 52, in the formula under "Example 13", change the " $\underset{H}{\overset{N}{|}}$ " to read -- N --

Col. 11, approximately line 16, in the formula under "Example 14", change the $\underset{H}{\overset{N}{|}}$ to read -- N -- and also change in that same formula "$(CH_2)_4$-" to read -- $(CH_2)_3$ --

Col. 25, line 27; "-butyrolacton)" should read -- -butyrolactone) --

Signed and Sealed this

First Day of January, 1991

Attest:

HARRY F. MANBECK, JR.

Attesting Officer

Commissioner of Patents and Trademarks